United States Patent [19]

Olij

[11] Patent Number: Plant 5,553

[45] Date of Patent: Sep. 10, 1985

[54] ROSE PLANT-OLYCISO VARIETY

[75] Inventor: Huibert W. Olij, Pr De Kwakel, Netherlands

[73] Assignee: The Conard-Pyle Company, West Grove, Pa.

[21] Appl. No.: 560,920

[22] Filed: Dec. 13, 1983

[30] Foreign Application Priority Data

Oct. 13, 1981 [NL] Netherlands ..... R00 1081

[51] Int. Cl.[3] ..... A01H 5/00

[52] U.S. Cl. ..... Plt./22

[58] Field of Search ..... Plt./22

*Primary Examiner*—Robert E. Bagwill

*Attorney, Agent, or Firm*—Burns, Doane, Swecker & Mathis

[57] ABSTRACT

A new rose plant of the Floribunda Class is provided having attractive bicolor semi-double flowers. Such flowers are china pink on the inside and whitish-cream suffused with china rose on the outside. The rose plant is particularly suitable for forcing under greenhouse conditions to abundantly yield cut flowers. Under such growing conditions, commonly one flower is formed per stem; however, additional blossoms per stem may be produced particularly when grown out-of-doors and/or during the spring.

17 Drawing Figures

SUMMARY OF THE INVENTION

The object of the present invention is to provide a new variety of rose plant of the Floribunda Class which is distinguished from prior varieties by the following characteristics:

(a) from the physical point of view, the rose plant with light green wood has bicolor semi-double flowers which are china pink on the inside and whitish-cream suffused with china rose on the outside; and (b) from the biological point of view, the rose plant has vigorous vegetation, produces flowers in abundance and particularly is amenable to greenhouse forcing, is not particularly susceptible to diseases, and forms long lasting flowers comprising petals which detach cleanly.

In view of these characteristics the new variety meets the needs of the horticultural industry, and particularly is suited for the production of long lasting cut flowers. Accordingly, the rose plant of the present variety may be classified as being a member of the Sweetheart Class. However, when the rose plant is grown out-of-doors it commonly exhibits typical Floribunda characteristics such as multiple buds per stem.

The new variety was created by artificial pollination whereby two parents which previously had been studied for the possession of the characteristics sought in the new variety were combined.

The seed parent of the new variety was the variety MERKO (non-patented) and the male parent was the variety MINUETTE (U.S. Plant Pat. No. 3,162).

The seeds resulting from the above pollination were sown and plantlets were obtained which were physically and biologically different from each other. Selective study resulted in the identification of a single plant of the new variety. Extensive testing has confirmed the behavior and chracteristics of the new variety which is particularly suited for the abundant production in a greenhouse of long lasting cut flowers having a distinctive bicolor appearance.

The characteristics and properties of the new variety have been found to be fully transmissible by agamic means, also called "asexual", i.e., by means of vegetative propagation, in particular by bench grafting, field budding, etc. on various understocks.

The rose plant of the new variety has been designated the OLYCISO variety.

BRIEF DESCRIPTION OF THE PHOTOGRAPH

The accompanying photograph shows typical specimens of plant parts and foliage of the present variety obtained from two-year old plants growing on Rosa indica understock during June in a greenhouse at Cap d'Antibes, France. The color shown is as nearly true as it is reasonably possible to make the same in a color illustration of this character.

DETAILED DESCRIPTION

Figures 1, 2, 3, 4, 5, 6, 7, 8, 9, 10, 11, 12, 13, 14, 15, 16, 17:
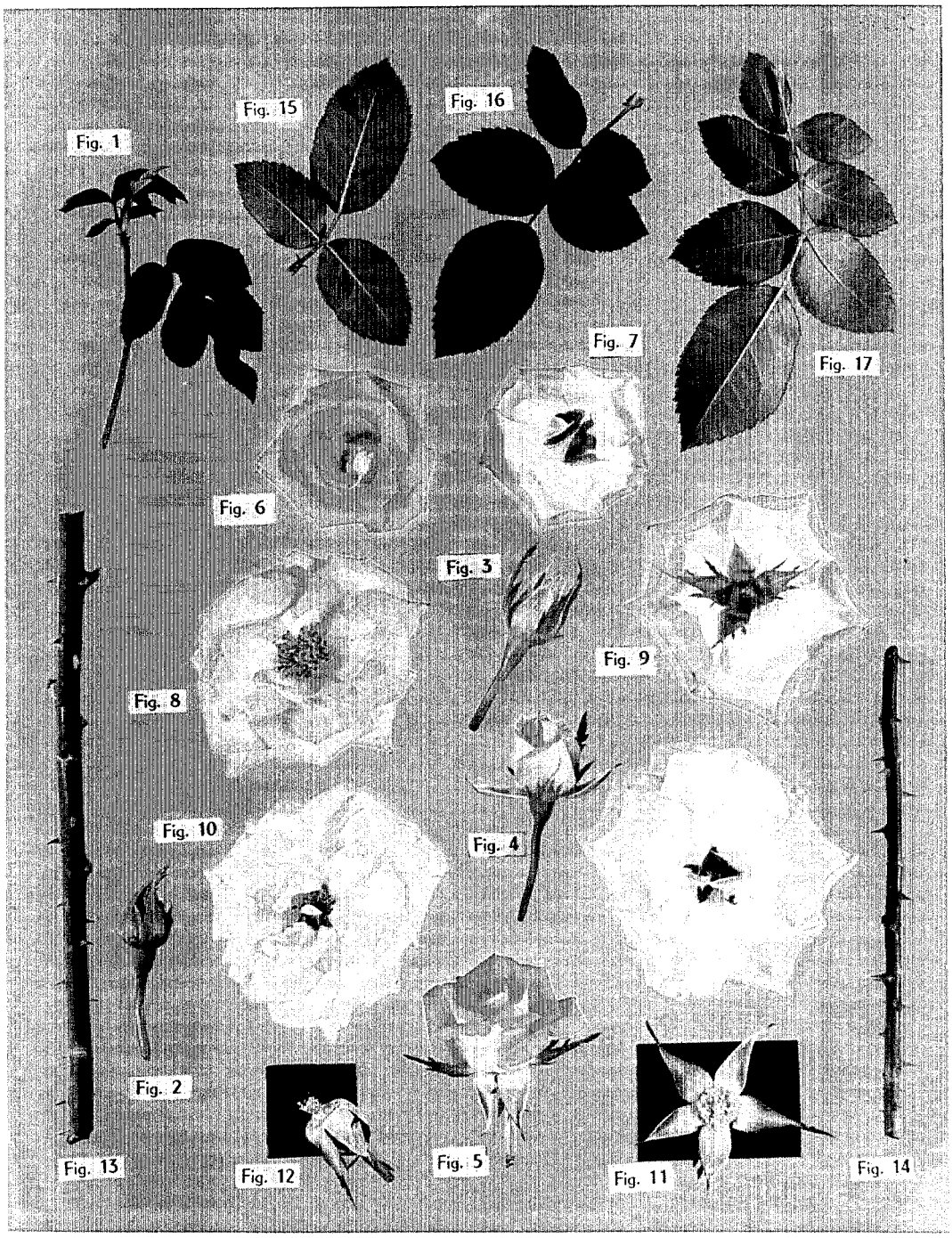
FIG. 1 is a specimen of young shoot.
FIG. 2 is a specimen of a bud before the opening of the sepals.
FIG. 3 is a specimen of a bud at the opening of the sepals.
FIG. 4 is a specimen of a bud at the opening of the petals.
FIG. 5 is a specimen of a recently opened flower.
FIG. 6 is a specimen of a half-open flower — plan view — obverse.
FIG. 7 is a specimen of a half-open flower — plan view — reverse.
FIG. 8 is a specimen of a fully open flower — plan view — obverse.
FIG. 9 is a specimen of a fully open flower — plan view — reverse.
FIG. 10 is a specimen of a fully open flower just prior to petal drop — plan view — obverse; the reverse is also shown, next to FIG. 4, but is not numbered.
FIG. 11 is a specimen of the stamen arrangement after the petals have been removed.
FIG. 12 is a specimen of the pistil arrangement after the petals and stamens are removed.
FIG. 13 is a specimen of a main branch from which flowering stems will grow.
FIG. 14 is a specimen of a flowering stem.
FIG. 15 is a specimen of a leaf with three leaflets, under surface.
FIG. 16 is a specimen of a leaf with five leaflets, upper surface.
FIG. 17 is a specimen of a leaf with seven leaflets, under surface.

The plants described were grown on Rosa indica understock during June in a greenhouse at Cap d'Antibes, France.

The chart utilized in the identification of the colors is that of The Royal Horticultural Society (R.H.S. Colour Chart).

Class: Floribunda.

Plant:

*Height.*—On the basis of the cutting back of the plants in greenhouses to approximately 0.85 m., the length of the cut flower bearing stems reaches approximately 30 to 40 cm.

*Bearing.*—Erect.

Branches:

*Color.*—Young stems: Light green 146B (Yellow-Green Group). Mature wood: Light green 146B (Yellow-Green Group) with some reddish blush.

*Prickles.*—Upper edge: Straight with slight curve at base. Under edge: Slightly concave. Size: Average. Quantity: Average on lower part of plant, but less on flower bearing stems. Color on young stems: Reddish at base and become greenish at tip. Color on mature wood: Havana brown.

Leaves:

*Stipules.*—Adnate, pectinate, fairly narrow and linear.

*Petioles.*—Inner surface: grooved, reddish, brown (young foliage) and medium green more or less suffused with red (adult foliage) with more or less glandular edges.

*Folioles.*—Number: three, five (most often), and occasionally seven. Sometimes the first pair of leaflets is incomplete. Shape: Elliptical with symmetrical round base and an acuminate apex. Teeth: Simple and very regular. General effect: Foliage is ample, dense, and has a fairly dull appearance.

*Color.*—Young foliage: Upper surface: Reddish brown. Under surface: Reddish brown Adult foliage: Upper surface: Dark green 147A (Yellow-Green Group). Under surface: Light green 147B (Yellow-Green Group) and somewhat suffused with a rouge tinge.

Inflorescence:

*Number of flowers.*—Commonly one flower per stem when grown in a greenhouse; however, additional blossoms (e.g. up to approximately four per stem or more) may be produced particularly when grown out-of-doors and/or during the spring.

*Peduncle.*—Erect, rigid, slightly glandular.

*Sepals.*—Upper surface: Tomentose, greenish. Under surface: Light green, very slightly glandular. The outer sepals have a few appendages at their edges.

*Bud.*—Shape: Oblong. Length: Approximately 2.5 cm. on average. Width: Slender. Color when opening begins: Upper surface: Red-Purple Group 58B on outside petals and Red-Purple Group 57A towards the center. Under surface: Whitish with a margin of Red-Purple Group 58B which suffuses to Red-Purple Group 58C toward the center of the petal.

*Flower.*—Shape: Initially with parallel sides and subsequently in the form of a hollow cup, semi-double flower. Diameter: Approximately 8 cm. on average. Color when first opening: Upper surface: Red-Purple Group 58B becoming lighter at the base of the petal where yellowish coloration is present. Under surface: Red-Purple Group 58D suffused with Red Group 55D Color during the course of opening: Upper surface: Red-Purple Group 58C breaking down to Red-Purple Group 58D. Under surface: Whitish suffused to a large degree with Red Group 55D. Color just before petal drop: Upper surface: Red-Purple Group 64D and becoming lighter near the base of the petal. Under surface: Whitish with some tones of Gray-Purple Group 186C. Fragrance: None. Lasting quality: Average to good. Corolla: Petals: Texture: Firm. Shape: Rounded; the tip of the outside petals may be notched. Number: Approximately 18 on average. Shedding petals: The petals drop off cleanly. Stamens: Number: Approximately 131 on average. Anthers: Usual, yellow in coloration. Filaments: Bright yellow, irregular in height. Pistils: Number: Approximately 43 on average. Stigmas: Normal, straw colored. Styles: Twisted, fuchsia at top, irregular in height. Receptacle: Light green at the dehiscence of the anthers, and in longitudinal section it is narrow and in the shape of a jug.

Development:

*Vegetation.*—Vigorous.

*Flowering.*—Abundant.

*Aptitude to forcing.*—Very good.

*Resistance to diseases.*—Good.

I claim:

1. A new and distinct vareity of Floribunda rose plant of vegetative reproduction substantially as illustrated and described by the fact that:

(a) from the physical point of view, the rose plant with light green wood has bicolor semi-double flowers which are china pink on the inside and whitish-cream suffused with china rose on the outside; and (b) from the biological point of view, the rose plant has vigorous vegetation, produces flowers in abundance and particularly is amenable to greenhouse forcing, is not particularly susceptible to diseases, and forms long lasting flowers comprising petals which detach cleanly.

* * * * *